United States Patent
Tsukamoto et al.

(10) Patent No.: US 7,002,043 B2
(45) Date of Patent: Feb. 21, 2006

(54) PROCESS FOR PRODUCING 1,1,1-TRIFLUOROACETONE

(75) Inventors: Masanori Tsukamoto, Yamaguchi (JP);
Fumiyoshi Yoshikawa, Saitama (JP);
Masataka Fujimoto, Saitama (JP);
Naoto Takada, Saitama (JP);
Yoshikazu Sugimori, Saitama (JP);
Junji Negishi, Saitama (JP)

(73) Assignee: Central Glass Company, Limited, Ube (JP)

(*) Notice: Subject to any disclaimer, the term of this patent is extended or adjusted under 35 U.S.C. 154(b) by 90 days.

(21) Appl. No.: 10/448,318

(22) Filed: May 30, 2003

(65) Prior Publication Data
US 2004/0034254 A1 Feb. 19, 2004

(30) Foreign Application Priority Data
May 31, 2002 (JP) .............................. 2002-158570

(51) Int. Cl.
C07C 45/65 (2006.01)

(52) U.S. Cl. ....................................... 568/394; 568/411

(58) Field of Classification Search ................ 568/394, 568/411
See application file for complete search history.

(56) References Cited

U.S. PATENT DOCUMENTS

| 6,177,595 B1 * | 1/2001 | Nadano et al. ............. 568/394 |
| 6,262,312 B1 | 7/2001 | Goto ........................... 568/394 |
| 6,340,776 B1 | 1/2002 | Goto et al. ................. 568/394 |

FOREIGN PATENT DOCUMENTS

| JP | 63280035 | 11/1988 |
| JP | 10287609 | 10/1998 |
| JP | 11001451 | 1/1999 |
| JP | 2000-336057 | 12/2000 |
| JP | 2001-316322 | 11/2001 |

OTHER PUBLICATIONS

Mark Cushman, et al., "Synthesis of Trifluromethylated Pyrazine-Containing Nitrogen Heterocycles from Trifuromethylated and Ortho-Diamines: Scope and Regiochemistry" J. Org. Chemistry, vol. 53, pp. 5088-5092, 1988.

* cited by examiner

Primary Examiner—Sikarl A. Witherspoon
(74) Attorney, Agent, or Firm—Crowell & Moring LLP

(57) ABSTRACT

The invention relates to a process for producing 1,1,1-trifluoroacetone, which is useful as an intermediate of pharmaceuticals and agricultural chemicals, or as a reagent for introducing fluorine-containing groups. This process includes the step of conducting a hydrogenolysis of a halogenated trifluoroacetone, which is represented by the formula [1], by a hydrogen gas, in a liquid phase containing water, in the presence of a catalyst containing a transition metal,

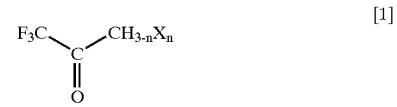

[1]

where X represents a chlorine, bromine or iodine, and n represents an integer from 1 to 3. It is possible by the process to easily produce 1,1,1-trifluoroacetone with high purity.

18 Claims, No Drawings

PROCESS FOR PRODUCING 1,1,1-TRIFLUOROACETONE

BACKGROUND OF THE INVENTION

The present invention relates to a process for producing 1,1,1-trifluoroacetone, which is useful as an intermediate of pharmaceuticals and agricultural chemicals, or as a reagent for introducing fluorine-containing groups.

Japanese Patent Laid-open Publication 2000-336057, corresponding to U.S. Pat. No. 6,262,312, discloses a process for industrially producing 1,1,1-trifluoroacetone by subjecting a halogenated trifluoroacetone, which is represented by the formula [1], to a reduction treatment in the presence of a metallic zinc (as a reducing agent) and a protonic solvent,

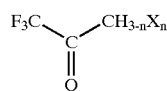
[1]

where X represents a chlorine, bromine or iodine, and n represents an integer from 1 to 3.

Japanese Patent Laid-open Publication 2001-316322, corresponding to U.S. Pat. No. 6,340,776, discloses another process for producing 1,1,1-trifluoroacetone without necessity of using a large amount of metallic zinc. In this process, a halogenated trifluoroacetone of the formula [1] is subjected to a hydrogenolysis in a gas phase using a solid-phase catalyst containing a particular transition metal, while the halogenated trifluoroacetone is kept in a vaporized condition. It is disclosed in this publication that an example of the halogenated trifluoroacetone is 1,1-dichloro-3,3,3-trifluoroacetone.

Japanese Patent Laid-open Publication 10-287609 discloses a first process for producing 1,1-dichloro-3,3,3-trifluoroacetone by fluorinating pentachloroacetone by hydrogen fluoride in a liquid phase in the presence of an antimony catalyst.

Japanese Patent Laid-open Publication 11-001451 discloses a second process for producing 1,1-dichloro-3,3,3-trifluoroacetone by fluorinating pentachloroacetone by hydrogen fluoride in a gas phase in the presence of an aluminum catalyst.

SUMMARY OF THE INVENTION

In producing a 3-halogenated-1,1,1-trifluoroacetone (i.e., the halogenated trifluoroacetone of the formula [1], such as 1,1-dichloro-3,3,3-trifluoroacetone) by the above-mentioned first or second conventional method, a difluoroacetone derivative represented by the formula [2] is produced as a by-product,

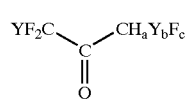
[2]

where Y represents a chlorine, bromine or iodine, a represents an integer from 0 to 2, b represents an integer from 0 to 3, c represents 0 or 1, and (a+b+c)=3.

It is difficult to remove the difluoroacetone derivative of the formula [2] from the halogenated trifluoroacetone by purification such as distillation. Therefore, it is practical and economically advantageous to use such a halogenated trifluoroacetone (containing as an impurity about 0.01–5 wt % of the difluoroacetone derivative) as a raw material for producing 1,1,1-trifluoroacetone.

For example, such a halogenated trifluoroacetone of the formula [1] (containing as an impurity the difluoroacetone derivative of the formula [2]) can be subjected to a hydrogenolysis in accordance with Japanese Patent Laid-open Publication 2001-316322 in a gas phase where the halogenated trifluoroacetone is kept in a vaporized condition. In this hydrogenolysis, the halogenated trifluoroacetone is turned into the target compound 1,1,1-trifluoroacetone, while the difluoroacetone derivative is also subjected to hydrogenolysis into 1-halogenated-1,1-difluoroacetone (represented by the formula [3]) and further into 1,1-difluoroacetone (represented by the formula [4]),

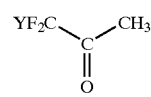
[3]

where Y represents a chlorine, bromine or iodine.

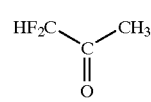
[4]

Of these compounds of the formulas [3] and [4], 1,1-difluoroacetone of the formula [4] forms an azeotropic mixture with 1,1,1-trifluoroacetone. Therefore, it is difficult to separate these compounds from each other by distillation. In other words, it is not easy to obtain 1,1,1-trifluoroacetone of high purity (containing a substantially low amount of 1,1-difluoroacetone) by the above-mentioned conventional process.

It is therefore an object of the present invention to provide a process for easily producing 1,1,1-trifluoroacetone of high purity.

According to the present invention, there is provided a process for producing 1,1,1-trifluoroacetone. This process comprises conducting a hydrogenolysis of a halogenated trifluoroacetone, which is represented by the formula [1], by a hydrogen gas, in a liquid phase containing water, in the presence of a catalyst comprising a transition metal (hereinafter it may be referred to as "transition metal catalyst" for simplification),

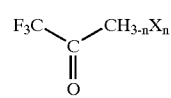
[1]

where X represents a chlorine, bromine or iodine, and n represents an integer from 1 to 3. Hereinafter, this hydrogenolysis of the present invention may be referred to as the liquid-phase hydrogenolysis.

DESCRIPTION OF THE PREFERRED EMBODIMENTS

A hydrogenolysis of the halogenated trifluoroacetone (represented by the formula [1]) by a hydrogen gas in the presence of a transition metal catalyst was conducted by the inventors in a liquid phase containing water. With this, we unexpectedly found that it is possible to synthesize 1,1,1-trifluoroacetone with high selectivity under a mild reaction condition. Herein, the reaction (hydrogenolysis) in a liquid phase containing water can refer to the following steps. At first, the halogenated trifluoroacetone is dissolved in water to produce a mixture. Then, the reaction (hydrogenolysis) is conducted, while this mixture is kept in the form of liquid. In other words, the reaction can be conducted by bringing the hydrogen gas into contact with the mixture in the presence of the transition metal catalyst, while the temperature of the mixture is set to be lower than its boiling point under the actual pressure.

In general, a halogenated hydrogen (e.g., HCl) is produced as a by-product in hydrogenolysis of a halide. In a continuous gas-phase hydrogenolysis (see Japanese Patent Laid-open Publication 2001-316322), the resulting halogenated hydrogen little affects the equilibrium and the catalyst, since the halogenated hydrogen is discharged from the reaction system together with the reaction product. In contrast, when this reaction is conducted in a liquid phase, the resulting halogenated hydrogen accumulates in the reaction system, thereby affecting the chemical equilibrium and the catalytic activity and consequently severely damaging the reaction. Thus, in case that hydrogenolysis of a halide is conducted in a liquid phase, it has been necessary to conduct the reaction in the presence of base in an amount by mol that is equal to or greater than that of the halogenated hydrogen (see Japanese Patent Laid-open Publication 63-280035).

However, when the halogenated trifluoroacetone of the formula [1] is brought into contact with base, it is hydrolyzed into aldehyde or the like (see J. Org. Chem. 1988, 53, pp. 5088–5092), thereby lowering 1,1,1-trifluoroacetone in yield and purity. Therefore, it is not preferable to conduct a liquid-phase hydrogenolysis of the halogenated trifluoroacetone in the presence of base.

In view of this, the inventors have tried to add water (in place of base) to the reaction system in a liquid-phase hydrogenolysis of the halogenated trifluoroacetone. Consequently, we unexpectedly found that the use of water in place of base makes the aimed hydrogenolysis proceed with high conversion and high selectivity and with suppression of its decomposition (hydrolysis) into aldehyde or the like.

Furthermore, we unexpectedly found that the production of the above-mentioned 1,1-difluoroacetone of the formula [4] is significantly suppressed in a hydrogenolysis of the halogenated trifluoroacetone of the formula [1] (containing as an impurity a difluoroacetone derivative of the formula [2]), although the difluoroacetone derivative is turned by its hydrogenolysis into 1-halogenated-1,1-difluoroacetone. Consequently, we found that it is possible by the liquid-phase hydrogenolysis of the present invention to easily obtain 1,1,1-trifluoroacetone of high purity (containing an extremely less amount of 1,1-difluoroacetone as compared with a conventional gas-phase hydrogenolysis). Furthermore, the liquid-phase hydrogenolysis of the present invention can have great advantages in producing 1,1,1-trifluoroacetone industrially, as explained in detail hereinafter.

The raw material in the hydrogenolysis of the present invention, that is, the halogenated trifluoroacetone of the formula [1], can be selected from 1,1-dichloro-3,3,3-trifluoroacetone, 1-chloro-3,3,3-trifluoroacetone, 1,1,1-trichloro-3,3,3-trifluoroacetone, 1,1-dibromo-3,3,3-trifluoroacetone, 1-bromo-3,3,3-trifluoroacetone, 1,1,1-tribromo-3,3,3-trifluoroacetone, 1,1,1-trifluoro-3,3-diiodoacetone, 1,1,1-trifluoro-3-iodoacetone, and 1,1,1-trifluoro-3,3,3-triiodoacetone. These compounds can be used alone or in mixture. Of these, it is particularly preferable to use 1,1-dichloro-3,3,3-trifluoroacetone due to its easiness in availability.

Specific examples of the difluoroacetone derivative of the formula [2], which is contained as an impurity in the halogenated trifluoroacetone, are 1,3-dichloro-1,1-difluoroacetone, 1-chloro-1,1,3-trifluoroacetone, 1,3-dichloro-1,1,3-trifluoroacetone, 1,1,3-trichloro-1,3,3-trifluoroacetone, 1,1,3-trichloro-3,3-difluoroacetone, 1,1,1,3-tetrachloro-3,3-difluoroacetone, 1,3-dibromo-1,1-difluoroacetone, 1-bromo-1,1,3-trifluoroacetone, 1,3-dibromo-1,1,3-trifluoroacetone, 1,1,3-tribromo-1,3,3-trifluoroacetone, 1,1,3-tribromo-3,3-difluoroacetone, 1,1,1,3-tetrabromo-3,3-difluoroacetone, 1,1-difluoro-1,3-diiodoacetone, 1,1,3-trifluoro-1-iodoacetone, 1,1,3-trifluoro-1,3-diiodoacetone, 1,3,3-trifluoro-1,1,3-triiodoacetone, 3,3-difluoro-1,1,3-triiodoacetone, and 3,3-difluoro-1,1,1,3-tetraiodoacetone. As stated above, the difluoroacetone derivative of the formula [2] is produced as a by-product in producing the halogenated trifluoroacetone of the formula [1]. Therefore, the group Y in the formula [2] usually corresponds to the group X in the formula [1]. For example, in case that the halogenated trifluoroacetone is 1,1-dichloro-3,3,3-trifluoroacetone, the difluoroacetone derivative usually becomes 1,3-dichloro-1,1,3-trifluoroacetone, 1,1,3-trichloro-1,3,3-trifluoroacetone or the like. However, the hydrogenolysis of the present invention is not interrupted, even if the halogenated trifluoroacetone of the formula [1] contains a halogenated 1,1-difluoroacetone (i.e., the difluoroacetone derivative) in which the group Y does not correspond to the group X of the formula [1].

The content of the difluoroacetone derivative(s) in total in the halogenated trifluoroacetone(s) in total is not particularly limited. It may be about 0.01–5 wt %, in case that the halogenated trifluoroacetone has been synthesized by the first conventional process of Japanese Patent Laid-open Publication 10-287609 or by the second conventional process of Japanese Patent Laid-open Publication 11-001451. It is preferably 2 wt % or less, since the less the difluoroacetone derivative is contained therein the less 1,1-difluoroacetone is produced.

The hydrogenolysis of the present invention can be achieved as follows. At first, the halogenated trifluoroacetone is dissolved in water to make a mixture. Then, while the mixture is kept in the form of liquid, it is brought into contact with hydrogen gas in the presence of a transition metal catalyst, followed by heating. In fact, it is possible to keep the mixture in the form of liquid by conducting the reaction under a pressurized and sealed condition using a reactor such as autoclave.

As stated above, the use of water is essential in the reaction of the present invention. Although the amount of water used in the reaction is not particularly limited, it is preferably 4 moles or more, more preferably 10 moles or more, per mole of the halogenated trifluoroacetone(s) in total. If it is less than 4 moles, conversion may become inferior. Although it does not have a particular upper limit, the reaction is not improved further by adding more than 30 moles of water.

In case that the raw material mixture in the hydrogenolysis contains a plurality of compounds corresponding to the halogenated trifluoroacetone of the formula [1], it is possible to set the amount of water, as follows. At first, the chemical composition of the raw material mixture is determined by an analysis such as gas chromatography. Then, the amount of each compound by mole can be determined by the expression of [the weight (g) of the raw material mixture]×[(the gas chromatographic percentage (%) of each compound)÷100 (%)]÷[the molecular weight of the corresponding compound]. Then, the amount of water is set, based on the total number of moles of all the compounds corresponding to the halogenated trifluoroacetone of the formula [1].

As stated above, the halogenated trifluoroacetone has a property to decompose into aldehyde or the like when it comes into contact with base. Therefore, it is not preferable to conduct the hydrogenolysis of the present invention in the presence of base. Examples of this base are inorganic base compounds (e.g., NaOH, KOH, LiOH, $Ca(OH)_2$, $Mg(OH)_2$, $K_2CO_3$, $Na_2CO_3$, $Li_2CO_3$, and $CaCO_3$) and organic base compounds (e.g., triethylamine and pyridine).

It is necessary in the hydrogenolysis to use a catalyst comprising a transition metal. This transition metal can be supported on a carrier. This transition metal is preferably palladium, platinum, ruthenium, iridium, or rhodium, since these elements do not easily corrode under reaction conditions of the hydrogenolysis and are high in catalytic activity. Of these, palladium is particularly preferable, since it is easy in handling and high in activity. These transition metals may be used in combination, too. The carrier for supporting the transition metal may be activated carbon, silica or alumina, preferably activated carbon. The way of making the transition metal to be supported on the carrier is not particularly limited. For example, it is possible to immerse a carrier in a solution of a transition metal compound or to spray this solution to a carrier, followed by drying and then reduction by hydrogen gas with heating at a temperature of about 150–350° C. Although the resulting catalyst itself may be used in the hydrogenolysis, it is preferable to mix the catalyst with a suitable amount of water to make a wet catalyst due to its easy handling. Furthermore, it is also possible to use a commercial catalyst such as one containing palladium supported on activated carbon.

The amount of the transition metal (in terms of the transition metal atom) to be supported on the carrier is not particularly limited. It may be in an amount of 0.1–10 g, preferably 0.2–5 g, per 100 g of the carrier. If it is less than 0.1 g, the reaction rate may become too slow. If it exceeds 10 g, the reaction may become inferior from the economical viewpoint. It is preferable to use the catalyst in an amount (except the weight of the water used for making a wet catalyst) of 0.1–30 wt %, preferably 1–10 wt %, based on the total weight of the halogenated trifluoroacetone of the formula [1]. Since the catalyst used in the hydrogenolysis is a solid-phase catalyst, it may be reused by separation from the reaction liquid through filtration or the like after its use in the hydrogenolysis.

Although specific steps for conducting the hydrogenolysis are not particularly limited, they can be conducted exemplarily as follows. At first, a pressure-proof autoclave is charged with a raw material mixture (containing the halogenated trifluoroacetone of the formula [1]) and water. This autoclave preferably has an inner wall made of a material (e.g., polytetrafluoroethylene and glass) that is corrosion-resistant under acidic condition. After adding a predetermined amount of the transition metal catalyst to the autoclave, the autoclave is sealed, and stirring of the mixture is started. Then, hydrogen gas is introduced from its cylinder into the autoclave to pressurize the same, followed by heating. During the reaction, hydrogen gas is supplied continuously or intermittently in a manner that the autoclave has a predetermined inside pressure. It is preferable to conduct the reaction while the progress of the reaction is checked at suitable intervals by sampling and analysis (e.g., NMR and gas chromatography) of the sample. With this checking, the reaction is continued until the raw material sufficiently turns into the target product or until the hydrogen gas is not absorbed any longer.

The reaction temperature may be from 50 to 150° C., preferably 70–120° C. The hydrogen gas pressure in the reaction system may be from 0.1 to 10 MPa, preferably 0.5–2.0 MPa. Although too-high pressure is not problematic in terms of reactivity, it may not be preferable in terms of industrial production, for example, due to demand for the reactor to have an excessively high strength. For example, in case that the reactor is made of glass, the upper limit of the hydrogen gas pressure may be about 2 MPa. Therefore, it is also preferable to suitably set the hydrogen gas pressure in view of strength of the reactor.

The process for isolating 1,1,1-trifluroacetone from the reaction mixture obtained by the reaction is not particularly limited and may be conducted exemplarily as follows. At first, a base (e.g., calcium hydroxide and sodium hydroxide) is added to the reaction mixture in a manner that the base is in an amount by mol that is equal to that of the halogenated hydrogen (e.g., HCl) produced as a by-product in the reaction, in order to neutralize the reaction mixture. Then, a dehydrating agent (e.g., calcium chloride, magnesium sulfate, and zeolite) is added to the reaction mixture. After that, the reaction mixture is subjected to distillation to isolate 1,1,1-trifluoroacetone as a distillate. After the above neutralization, the reaction mixture may be extracted with a common organic solvent (e.g., diethyl ether, benzene, toluene, and xylene), in place of adding a dehydrating agent thereto. Then, this solvent is distilled away from the organic layer, followed by distillation to isolate 1,1,1-trifluoroacetone. As mentioned hereinabove, the use of an organic solvent is not essential in the process for isolating 1,1,1-trifluoroacetone.

As stated above, although the 1-halogenated-1,1-difluoroacetone of the formula [3] (i.e., 1-chloro-1,1-difluoroacetone, 1-bromo-1,1-difluoroacetone, or 1-iodo-1,1-difluoroacetone) is generated in the hydrogenolysis from the difluoroacetone derivative of the formula [2], the production of 1,1-difluoroacetone of the formula [4] is extremely low. Thus, it is possible by the present invention to very easily obtain 1,1,1-trifluoroacetone with high purity, since the 1-halogenated-1,1-difluoroacetone can easily be separated from 1,1,1-trifluoroacetone by distillation.

The following nonlimitative examples are illustrative of the present invention.

EXAMPLE 1

1,1,1-Trifluoroacetone Synthesis by Liquid-Phase Process

A 200-liter, glass-lined reactor was charged with 77.5 kg of water, 51.5 kg of a raw material mixture, and 2.5 kg of a 5% palladium/activated carbon catalyst (containing 50% of water), and then stirring was started. The raw material mixture was found by gas chromatography to contain 3.2% of 1-chloro-3,3,3-trifluoroacetone, 86.2% of 1,1-dichloro-3,3,3-trifluoroacetone, 9.3% of 1,1,1-trichloro-3,3,3-trifluoroacetone, 0.5% of 1,3-dichloro-1,3,3-trifluoroacetone, and 0.7% of 1,1,3-trichloro-1,3,3-trifluoroacetone. The above catalyst was prepared by loading palladium (in an amount of 5 wt % in terms of metallic palladium) onto activated carbon and then by mixing the obtained palladium/activated carbon with water in an amount that was the same weight as that of palladium/activated carbon. After stirring of the mixture was started, the inside atmosphere of the reactor was replaced with nitrogen and hydrogen gases, and then the temperature of the reactor was increased by hot water. Then, hydrogen gas was continuously introduced into the reactor in a manner to maintain the inside pressure of the reactor at 1.0 MPa. Under this condition, the reaction was conducted under heating for about 7 hr to maintain an inside temperature of 80–90° C. After confirming that the consumption of hydrogen gas had been stopped, the reaction was terminated. The obtained reaction mixture was in an amount of 130 kg and was found by gas chromatography to contain 97.6% of 1,1,1-trifluoroacetone, 0.04% of 1,1-difluoroacetone (hereinafter "1,1-DFA"), and 1.2% of 1-chloro-1,1-difluoroacetone (hereinafter "CDFA").

After the reaction, 19 kg of calcium hydroxide were gradually added to the reaction mixture with stirring. After adding 45 kg of calcium chloride, the reaction mixture was subjected to distillation, thereby obtaining 26.5 kg of an organic matter containing anhydrous 1,1,1-trifluoroacetone as a major component. Then, an extractive distillation was conducted by using a rectification tower of theoretical 10 stages, under normal pressure and at 23° C. at the top of the tower, thereby obtaining 24.5 kg of 1,1,1-trifluoroacetone. This product was found by gas chromatography to contain 99.9% of 1,1,1-trifluoroacetone, 10 ppm of 1,1-DFA, and 40 ppm of CDFA. The yield of 1,1,1-trifluoroacetone (after distillation) from the raw material was 78%.

EXAMPLE 2

1,1,1-Trifluoroacetone Synthesis by Liquid-Phase Process

A 2-liter, glass-lined reactor was charged with 576 g of water, 384 g of a raw material mixture, and 19 g of a 5% palladium/activated carbon catalyst (containing 50% of water), and then stirring was started. The raw material mixture was found by gas chromatography to contain 2.2% of 1-chloro-3,3,3-trifluoroacetone, 85.0% of 1,1-dichloro-3,3,3-trifluoroacetone, 10.5% of 1,1,1-trichloro-3,3,3-trifluoroacetone, 1.5% of 1,3-dichloro-1,1,3-trifluoroacetone, and 0.8% of 1,1,3-trichloro-1,3,3-trifluoroacetone. The catalyst was prepared by the same process as that of Example 1. After stirring of the mixture was started, the inside atmosphere of the reactor was replaced with nitrogen and hydrogen gases, and then the temperature of the reactor was increased by hot water. Then, hydrogen gas was continuously introduced into the reactor in a manner to maintain the inside pressure of the reactor at 1.0 MPa. Under this condition, the reaction was conducted under heating for about 8 hr to maintain an inside temperature of 80–90° C. After confirming that the consumption of hydrogen gas had been stopped, the reaction was terminated. The obtained reaction mixture was found by gas chromatography to contain 97.8% of 1,1,1-trifluoroacetone, 0.03% of 1,1-DFA, and 1.2% of CDFA.

After the reaction, 150 g of calcium hydroxide were gradually added to the reaction mixture with stirring. After adding 244 g of calcium chloride, the reaction mixture was subjected to distillation, thereby obtaining 187 g of an organic matter containing anhydrous 1,1,1-trifluoroacetone as a major component. Then, an extractive distillation was conducted in the same manner as that of Example 1, thereby obtaining 168 g of 1,1,1-trifluoroacetone. This product was found by gas chromatography to contain 99.9% of 1,1,1-trifluoroacetone, 20 ppm of 1,1-DFA, and 30 ppm of CDFA. The yield of 1,1,1-trifluoroacetone (after distillation) from the raw material was 71%.

COMPARATIVE EXAMPLE 1,1,1-Trifluoroacetone Synthesis by Gas-Phase Process

An aluminum tubular reactor (catalytic layer cross-section area: 5.7 cm$^2$; height: 30 cm) was charged with 240 ml of a 5% palladium/activated carbon catalyst that had been prepared by the same process as that of Example 1. Then, the reactor was heated to 150° C., while hydrogen gas was allowed to flow through the reactor at a rate of 0.8 liter/min by upflow. A raw material mixture having the same chemical composition as that of Example 1 was introduced into a vaporizer at a rate of 2.0 g/min, thereby vaporizing this mixture. The resulting vapor was mixed with hydrogen gas, and the resulting mixture was introduced into the reactor after the reactor's inside temperature became stable. Under this condition, the reaction was conducted continuously for 28 hr. During the reaction, liquid and gas flowing out of the reactor were introduced into 6072 g of circulating water cooled at 0° C., thereby collecting them. The collected product was in an amount of 9431 g, and its organic component composition was found by gas chromatography to contain 97.6% of 1,1,1-trifluoroacetone, 0.7% of 1,1-DFA, and 0.6% of CDFA.

After the reaction, calcium hydroxide was added to the above-collected product, and then 5,150 g of anhydrous calcium chloride were added for dehydrating the product, thereby obtaining anhydrous 1,1,1-trifluoroacetone.

Then, the obtained anhydrous 1,1,1-trifluroacetone was subjected to an extractive distillation in the same manner as that of Example 1, thereby collecting 1,356 g of 1,1,1-trifluoroacetone as a main distillate. This product was found by gas chromatography to contain 99.4% of 1,1,1-trifluoroacetone, 200 ppm of 1,1-DFA, and 50 ppm of CDFA. The yield of 1,1,1-trifluoroacetone (after distillation) from the raw material was 66%.

The entire disclosure of each of Japanese Patent Application No. 2002-158570 filed on May 31, 2002, including specification, claims and summary, is incorporated herein by reference in its entirety.

What is claimed is:

1. A process for producing 1,1,1-trifluoroacetone, comprising conducting a hydrogenolysis of a halogenated trifluoroacetone, which is represented by the formula [1], by a hydrogen gas, in a liquid phase containing water, in the presence of a catalyst comprising a transition metal,

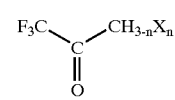

[1]

where X represents a chlorine, bromine or iodine, and n represents an integer from 1 to 3.

2. A process according to claim 1, wherein the halogenated trifluoroacetone contains as an impurity a difluoroacetone derivative represented by the formula [2],

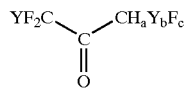

where Y represents a chlorine, bromine or iodine, a represents an integer from 0 to 2, b represents an integer from 0 to 3, c represents 0 or 1, and (a+b+c)=3.

3. A process according to claim 1, wherein the halogenated trifluoroacetone contains as an impurity a difluoroacetone derivative represented by the formula [2] or a 1-halogenated-1,1-difluoroacetone represented by the formula [3],

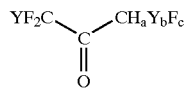

where Y represents a chlorine, bromine or iodine, a represents an integer from 0 to 2, b represents an integer from 0 to 3, c represents 0 or 1, and (a+b+c)=3,

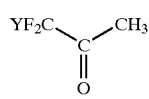

where Y represents a chlorine, bromine or iodine.

4. A process according to claim 1, wherein the water is in an amount of 4 moles or greater per mol of the halogenated trifluoroacetone.

5. A process according to claim 4, wherein the water is in an amount of 10 moles or greater per mol of the halogenated trifluoroacetone.

6. A process according to claim 1, wherein the hydrogenolysis is conducted at a temperature from 50 to 150° C., while the hydrogen gas is under a pressure from 0.1 to 10 MPa.

7. A process according to claim 1, wherein the transition metal is selected from the group consisting of palladium, platinum, ruthenium, iridium, and rhodium.

8. A process according to claim 1, wherein X of the formula [1] is the chlorine.

9. A process according to claim 2, wherein X of the formula [1] is the chlorine, and Y of the formula [2] is the chlorine.

10. A process according to claim 1, wherein the halogenated trifluoroacetone is 1,1-dichloro-3,3,3-trifluoroacetone.

11. A process according to claim 2, wherein the halogenated trifluoroacetone is 1,1-dichloro-3,3,3-trifluoroacetone, and
   wherein the difluoroacetone derivative is 1,3-dichloro-1,1,3-trifluoroacetone or 1,1,3-trichloro-1,3,3-trifluoroacetone.

12. A process according to claim 1, wherein the transition metal is palladium.

13. A process according to claim 1, wherein the catalyst further comprises a support for supporting thereon the transition metal.

14. A process according to claim 13, wherein the support is selected from the group consisting of activated carbon, silica, and alumina.

15. A process according to claim 1, wherein the hydrogenolysis is conducted in the absence of a base.

16. A process according to claim 1, wherein the transition metal of the catalyst is a palladium supported on an activated carbon.

17. A process according to claim 3, wherein the halogenated trifluoroacetone is 1,1-dichloro-3,3,3-trifluoroacetone,
   wherein the difluoroacetone derivative is 1,3-dichloro-1,1,3-trifluoroacetone or 1,1,3-trichloro-1,3,3-trifluoroacetone, and
   wherein the 1-halogenated-1,1-difluoroacetone is 1-chloro-1,1-difluoroacetone.

18. A process according to claim 1, wherein the hydrogenolysis is conducted by the steps of:
   (a) dissolving the halogenated trifluoroacetone in water to produce a mixture; and
   (b) bringing the hydrogen gas into contact with the mixture in the presence of the catalyst, while the mixture is kept in a form of liquid.

* * * * *